United States Patent [19]
Radunz et al.

[11] Patent Number: 5,095,114
[45] Date of Patent: Mar. 10, 1992

[54] PROCESS FOR THE ENANTIOMER-SELECTIVE PREPARATION OF γ-KETO-δ-AMINO ACID DERIVATIVES

[75] Inventors: Hans-Eckart Radunz, Mühltal; Hans U. Reissig, Darmstadt, both of Fed. Rep. of Germany

[73] Assignee: Merck Patent Gesellschaft Mit Beschränkter Haftung, Darmstadt, Fed. Rep. of Germany

[21] Appl. No.: 540,675

[22] Filed: Jun. 19, 1990

[30] Foreign Application Priority Data

Jun. 19, 1989 [DE] Fed. Rep. of Germany ....... 3919898

[51] Int. Cl.⁵ .................. C07C 229/00; C07D 455/02
[52] U.S. Cl. ............................... 544/224; 544/242; 546/138; 546/139; 548/469; 548/470; 560/16; 560/37; 560/153; 560/170; 562/567; 562/568
[58] Field of Search .................. 560/24, 160, 170, 37, 560/16, 153; 544/224, 242; 546/1, 138, 139; 548/400, 469, 470, 325; 562/567, 568

[56] References Cited

U.S. PATENT DOCUMENTS

| | | | |
|---|---|---|---|
| 3,711,458 | 1/1973 | Olofson et al. | 260/112.5 |
| 4,325,877 | 4/1982 | Metcalf et al. | 260/349 |
| 4,855,486 | 8/1989 | Kalbag | 560/158 |

FOREIGN PATENT DOCUMENTS 1-275553  11/1989  Japan .

OTHER PUBLICATIONS

Ewenson et al., J. Med. Chem., 29: 295–299 (1986).
Almquist et al., J. Med. Chem., 23: 1392–1398 (1980).
Araki et al., Bull. Chem. Soc. Jpn., 47: 1777–1780 (1974).
Lloyd et al., J. Chem. Soc. (C), 2890–2896 (1971).

*Primary Examiner*—Jose G. Dees
*Assistant Examiner*—Porfirio Nazario
*Attorney, Agent, or Firm*—Millen, White & Zelano

[57] ABSTRACT

The invention relates to a process for the enantiomer-selective preparation of γ-keto-δ-amino acid derivatives of the formula I

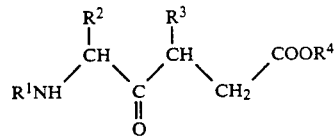

characterized in that a compound of the formula II

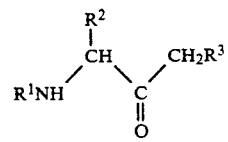

is converted, using a trialkylchlorosilane, into a compound of the formula III

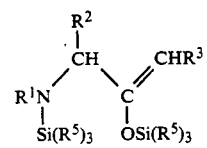

this compound is then reacted with a diazoacetate of the formula $N_2CH_2COOR^4$ ($R^4 \neq H$) to give a cyclopropane compound of the formula IV

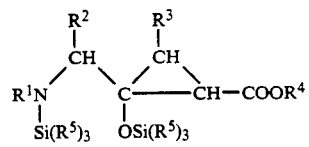

and then the compound IV is converted, by ring-opening and removal of the silyl groups, and where appropriate saponification, into the compound of the formula I, $R^1$, $R^2$, $R^3$, $R^4$ and $R^5$ having the meanings indicated in claim 1.

9 Claims, No Drawings

PROCESS FOR THE ENANTIOMER-SELECTIVE PREPARATION OF γ-KETO-δ-AMINO ACID DERIVATIVES

BACKGROUND OF THE INVENTION

The invention relates to a process for the enantiomer-selective preparation of γ-keto-δ-amino acid derivatives of the formula I

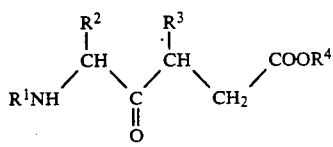

in which
R$^1$ is an amino-protective group or H,
R$^2$ is an alkyl group having 1 to 5 C atoms, which can optionally be mono- or di-substituted by —OH, —COOH, —CONH$_2$ or —NH$_2$, or in which a CH$_2$ group can optionally be replaced by —S—, phenyl or cyclohexyl which are unsubstituted or mono- or polysubstituted by alkyl or alkoxy containing 1 to 5 C atoms, halogen, hydroxyl or amino, or phenylalkyl or cylcohexylalkyl, or Het-alkyl, where Het is a saturated or unsaturated 5- or 6-membered heterocyclic radical having 1–4 N atoms, which can be fused with a benzene ring, and -alkyl is an alkylene group having 1–5 C atoms, and
R$^3$ and R$^4$ in each case independently of one another are H or alkyl having 1–5 atoms.

Compounds of the formula I are used as ketomethylene analogues of a dipeptide and are used as components in inhibitors of angiotensin converting enzyme, described by, for example, R. G. Almquist et al. in J. Med. Chem. 31, 561 (1988), or in tachykinin analogues, described by A. Ewenson et al. in J. Med. Chem. 29, 295 (1986).

The incorporation of these amino acids of the formula I and their reduced forms (γ-hydroxy-δ-amino acids) into other pharmacologically interacting peptides, such as, for example, inhibitors of the aspartyl proteases, is also possible.

Hitherto the enantiomer-selective preparation of γ-keto-δ-amino acids has been possible only to an unsatisfactory degree. For example, the synthesis of an optically active ketomethylene analogue of the dipeptide L-phenylalanylglycine is described by R. G. Almquist in J. Med. Chem. 23, 1392 (1980). This synthesis is carried out in 6 stages, a N-phthaloyl-L-phenylalanine 2-pyridyl-thioester first being reacted with 2-(2-magnesium-2-bromoethyl)-1,3-dioxolane to give the corresponding ketoacetal (cf. M. Araki et al., Bull. Chem. Soc. Jpn., 47, 1777 (1974) and K. Lloyd et al., J. Chem. Soc.C, 2890 (1971)). The keto group is then converted, analogously to the method of W. S. Johnson et al., J. Am. Chem. Soc., 78, 6289 (1956), to the ethylene ketal, and the phthaloyl group is subsequently subjected to a hydrazinolysis, followed by a benzoylation of the previously formed amine. Then in the 5th and 6th step of the synthesis the compound is first oxidized to the intermediate ketal acid and the ketal group is then removed using trifluoroacetic acid.

Another synthesis is described by A. Ewenson et al. in J. Med. Chem. 29, 295 (1986), in which, however, a mixture of enantiomers is formed.

Since for the effectiveness of such a product the (S)-configuration on the C atom that carries the —NHR$^1$ group is preferred, an enantiomer-selective synthesis is necessary.

The processes known hitherto have the disadvantage that they are not enantiomer-selective or that numerous time-consuming synthesis steps are necessary.

SUMMARY OF THE INVENTION

The object was, therefore, to find a process that enables valuable compounds of the formula I to be prepared in a simple and economic manner, with very high enantiomer selectivity and in a good yield.

Surprisingly it has now been found that ketoamino acids of the formula I can be obtained enantiomer-selectively by conversion of an appropriate aminoketone, via a silylenol ether, to the corresponding cyclopropane derivative with subsequent ring opening.

The subject of the invention is therefore a process for the enantiomer-selective preparation of γ-keto-δ-amino acid derivatives of the formula I, characterized in that a compound of the formula II

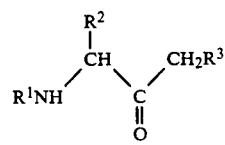

is converted, using a trialkylchlorosilane, into a compound of the formula III

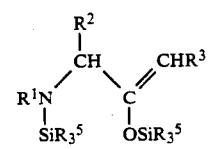

the compound of the formula III is then reacted with a diazoacetate of the formula N$_2$CH$_2$COOR$^4$ (R$^4$≠H) to give a cyclopropane compound of the formula IV

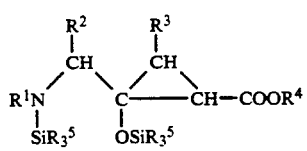

and the compound of the formula IV is then converted, by ring-opening and removal of the silyl groups, and where appropriate saponification, into the compound of the formula I, the groups R$^1$, R$^2$, R$^3$ and R$^4$ in the formulae II–IV having the meanings already indicated and R$^5$ being an alkyl group having 1 to 5 C atoms.

Unless expressly stated otherwise, in the preceding and following text the radicals R$^1$, R$^2$, R$^3$, R$^4$ and R$^5$ have the stated meanings.

According to the invention alkyl or alkylene having 1–5 C atoms can be unbranched or branched. Alkyl is preferably methyl, ethyl, propyl, butyl or pentyl, but also isopropyl, isobutyl, sec.- or tert.-butyl, 3-methylbutyl, 1,1-, 1,2- or 2,2-dimethylpropyl or 1-ethylpropyl.

Alkylene is preferably methylene, ethylene, propylene, additionally also butylene or pentylene.

$R^1$ in the formulae I–IV is an amino-protective group which does not interfere in the reaction process or, after splitting off this group, is also H.

The expression "amino-protective group" is generally known and relates to groups which are suitable for protecting (blocking) an amino group against chemical reactions but which are easily removable after the desired chemical reaction has been carried out at another place in the molecule. Typical of such groups are, in particular, unsubstituted or substituted acyl, aryl (for example 2,4-dinitrophenyl DNP), aralkoxymethyl (for example benzyloxymethyl BOM) or aralkyl (for example, benzyl, 4-nitrobenzyl, triphenylmethyl) groups. Since the amino-protective groups are removed after the desired reaction (or sequence of reactions), their type and size is, however, not critical; however, amino-protective groups having 1–20, in particular 1–8 C atoms, are preferred. In connection with the present process, the expression "acyl group" is to be interpreted in the broadest sense. It includes acyl groups derived from aliphatic, araliphatic, aromatic or heterocyclic carboxylic acids or sulfonic acids and in particular alkoxycarbonyl, aryloxycarbonyl and especially aralkoxycarbonyl groups. Examples of such acyl groups are alkanoyl, such as acetyl, propionyl or butyryl; aralkanoyl, such as phenylacetyl; aroyl, such as benzoyl or toluyl; aryloxyalkanoyl, such as phenoxyacetyl; alkoxycarbonyl, such as methoxycarbonyl, ethoxycarbonyl (ETOC), 2,2,2-trichloroethoxycarbonyl, isopropoxycarbonyl (IPOC), tert.-butoxycarbonyl (BOC) or 2-iodoethoxycarbonyl; aralkyloxycarbonyl, such as benzyloxycarbonyl (CBZ), 4-methoxybenzyloxycarbonyl or 9-fluorenylmethoxycarbonyl (FMOC). Preferred amino-protective groups are BOC, DNP and BOM, and also CBZ, FMOC, benzyl and acetyl.

$R^2$ is preferably an alkyl group having the preferred meanings already indicated for such a group.

Alkyl groups which are mono- or di-substituted by —OH, —COOH, —CONH$_2$ or —NH$_2$ are also preferred for $R^2$.

Consequently the following radicals $R^2$ are also particularly preferred: —CH$_2$OH, —CH(OH)—CH$_3$, —CH$_2$COOH, —CH$_2$—CONH$_2$, —CH$_2$—CH$_2$—COOH, —CH$_2$—CH$_2$—CONH$_2$, —CH$_2$—CH$_2$—CH$_2$—NH$_2$, —CH$_2$—CH$_2$—CH$_2$—CH$_2$—NH$_2$.

In the alkyl groups for $R^2$ a CH$_2$ group can also be replaced by —S—.

Furthermore, unsubstituted or substituted phenyl, phenylalkyl, cyclohexyl or cyclohexylalkyl groups are preferred for $R^2$. These groups can be mono- or poly-substituted in the 2-, 3- and/or 4-position. A monosubstitution in the 4-position is preferred. In the case of substituted phenyl or phenylalkyl, preferred substituents are fluorine, chlorine, hydroxyl and alkyl or alkoxy having 1 to 5 C atoms. In the case of substituted cyclohexyl or cyclohexylalkyl, alkyl groups are preferred as substituents.

Phenylalkyl or cyclohexylalkyl are preferably phenylmethyl or cyclohexylmethyl, phenylethyl or cyclohexylethyl or also phenylpropyl or cyclohexylpropyl. Consequently the following groups are preferred: benzyl (phenylmethyl), cyclohexylmethyl, 1- 2-phenylethyl, 1- or 2-cyclohexylethyl, o-, m- or p-methylbenzyl, 1- or 2-o-, -m- or -p-tolyethyl, o-, m- or p-ethylbenzyl, 1- or 1-o-, -m- or -p-ethylphenylethyl, o-, m- or p-methoxybenzyl, 1- or 2-o-, -m- or -p-methoxyphenylethyl, o-, m- or p-fluorobenzyl, 1- or 2-o-, -m- or -p-fluorophenylethyl, o-, m- or p-chlorobenzyl, 1- or 2-o-, -m- or -p-chlorophenylethyl, o-, m- or p-bromobenzyl, 1- or 2-o-, -m- or -p-bromophenylethyl, o-, m- or p-iodobenzyl, 1- or 2-o-, -m- or -p-iodophenylethyl, o-, m- or p-hydroxybenzyl, 2,3-, 2,4-, 2,5-, 2,6-, 3,4- or 3,5-dimethoxybenzyl, 3,4,5-trimethoxybenzyl, o-, m- or p-aminobenzyl, 2-, 3- or 4-methylcyclohexylmethyl, 2-, 3- or 4-ethyl-cyclohexylmethyl, 2-, 3- 4-tert.butylcyclohexylmethyl or 1- or 2-(2-, (3- or (4-ethylcyclohexyl)-ethyl.

$R^2$ is also preferably Het-alkyl-.

Het is preferably 1-, 2- or 3-pyrrolyl, 1-, 2-, 3-, 4-, 5-, 6- or 7-indolyl, 1-, 2-, 3-, 4-, 5-, 6- or 7-isoindolyl, 1-, 3-, 4- or 5-pyrazolyl, 1-, 2-, 4- or 5-imidazolyl, 1-, 2-, 4- or 5-benzimidazolyl, 2-, 3- or 4-pyridyl, 2-, 4-, 5- or 6-pyrimidinyl, and furthermore preferably 3- or 4-pyridazinyl or pyrazinyl, quinolyl or isoquinolyl. The heterocyclic radicals can also be partially or completely hydrogenated and consequently are, for example, 2,3-dihydropyrrolyl, 2,5-dihydropyrrolyl, pyrrolidinyl, tetrahydroimidazolyl, 2,3-dihydropyrazolyl, tetrahydropyrazolyl, 1,4-dihydropyridyl, 1,2,3,4-tetrahydropyridyl, 1,2,3,6-tetrahydropyridyl or piperidinyl.

If $R^2$ contains functional groups, the latter are preferably protected, before carrying out the enantiomerselective synthesis, by appropriate protective groups known from the literature which are then subsequently removed again.

Several—identical or different—protected amino and/or hydroxyl groups can thus also be present in the molecule of the starting material. If the protective groups present differ from one another, they can, in many cases, be selectively removed.

The radicals $R^3$ and $R^4$ are H or alkyl having 1–5 C atoms. In this case suitable alkyl groups are the preferred groups already defined.

In the compound trialkylchlorosilane $R^5$ is an alkyl group having 1–5 C atoms having the preferred meanings already indicated for alkyl. Methyl or ethyl are the particularly preferred meanings.

The desired (R)- or (S)- enantiomer is used as the starting material and, with retention of the configuration, the corresponding product of the formula I in the (R)- or (S)- form is then obtained. The starting materials, the aminoketones of the formula II, are accessible using known methods of preparation, described, for example, in Chem. Pharm. Bull. 36, 3341 (1988) by S. Kano et al.

The first step of the synthesis, the preparation of the silyl enol ethers of the formula III from the aminoketones II, is carried out by reaction with a trialkylchlorosilane in the presence of a strong, organic base, such as, for example, a metal amide, lithium dialkylamide, or magnesium dialkylamide, in particular lithium diisopropylamide, using standard methods. Suitable solvents are, for example, tetrahydrofuran, dialkyl ethers, mixtures of tetrahydrofuran with alkanes, such as, for example, pentane or hexane, or mixtures of different ethers.

The reaction temperatures are preferably between −120° and −40°, in particular between −80° and −60°.

After completion of the reaction at these low temperatures (the reaction time can be between 30 minutes and 8–10 hours), the reaction mixture is preferably allowed to return slowly to normal temperature over a period of a few hours. The working-up is then carried out using standard methods.

The second step, the preparation of the cyclopropane derivatives of the formula IV, is carried out by addition of a diazoacetate of the formula $N_2CH_2COOR^4$, in which $R^4$ is alkyl having 1–5 C atoms, that is to say not H in this case, to the double bond of the compound of the formula III in the presence of a copper compound, preferably a copper salt or copper complex. Copper acetate, copper halides, bis-(salicylaldiminato)-copper complex and bis-(acetylacetonato)-copper(II) complex may be named as examples of such copper compounds. The bis-(acetyl-acetonato)-copper(II) compound is preferably used. In other respects this cycloaddition is carried out using standard methods, such as are described in the organic chemistry textbooks.

Preferably an inert aromatic solvent is used, for example benzene, toluene or xylene, and the reaction mixture is heated under reflux, preferably at 70°–100°, particularly preferentially at 80°, until the evolution of nitrogen has ceased.

These two synthesis stages are preferably carried out under a protective gas atmosphere.

The final synthesis step, the ring opening and simultaneous removal of the silyl groups, is carried out by reacting the cyclopropane derivatives of the formula IV in an inert solvent with a fluorine salt. Suitable solvents are halogenated hydrocarbons, such as, for example, dichloromethane or tetrachloromethane, or also hydrocarbons or ethers.

Suitable fluorine salts are, for example, metal fluorides such as NaF or KF, ammonium fluorides such as, for example, $Bu_4NF$, or also HF in the form of $NEt_3 \cdot HF$.

The reaction process is preferably carried out at temperatures between 10° and 100°, particular preferentially between 15° and 30°. Depending on the batch size, the reaction time is between 30 minutes and 10 hours. The working up is preferably carried out by extraction.

According to the invention the γ-keto-δ-amino acid derivatives of the formula I are obtained using customary simple working-up and purification techniques, for example by means of chromatography and/or crystallization.

If desired, the amino-protective group $R^1$ can then be removed using methods known from the literature, in which case $R^1=H$. Where appropriate the ester group $-COOR^4$ can also be saponified, in which case $R^4=H$ in formula I.

Using the process according to the invention, these valuable ketomethylene analogues of a dipeptide can now be prepared with high stereo-selectivity and in good yields.

For example, the ketomethylene analogues of the following dipeptides can be prepared using the process according to the invention: Phe-Gly, Ala-Gly, Val-Gly, Leu-Gly, Ile-Gly, Ser-Gly, Thr-Gly, Asx-Gly, Lys-Gly, His-Gly, Met-Gly, Tyr-Gly, Trp-Gly or also Orn-Gly.

The abbreviations have the following meaning:
Phe=phenylalanine
Gly=glycine
Ala=alanine
Val=valine
Leu=leucine
Ile=isoleucine
Ser=serine
Thr=threonine
Asx=asparagine or aspartic acid
Lys=lysine
His=histidine
Met=methionine
Tyr=tyrosine
Trp=tryptophan and
Orn=ornithine Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight. The term "m.p." refers to melting point.

The entire disclosures of all applications, patents and publications, if any, cited above and below, and of corresponding application(s) Fed. Rep. of Germany P 39 19 898.7, filed June 19, 1989, are hereby incorporated by reference.

EXAMPLE 1 a) 2.00 g (7.60 mmol) of 1-(N-tert.-butyloxycarbonyl-amino)-2-(S)-phenylethyl methyl ketone (preparation analogous to the method of S. Kano et al., Chem. Pharm. Bull. 36, 3341 (1988)) in 30 ml of THF are added at −78° to a lithium diisopropylamide solution (prepared at −78° from 1.93 g (19.00 mmol) of diisopropylamine and 7.6 ml (19.00 mmol) of n-butyl-lithium in hexane (2.5 M) under a protective-gas atmosphere. The mixture is stirred for approximately 2 hours at −78° and 2.47 g (22.80 mol) of trimethylchlorosilane are then added, the mixture is allowed to return to room temperature overnight, a little dry triethylamine is added and the solvent is removed. 20 ml of pentane are added to the residue, the precipitated solid is filtered off, the filtrate is concentrated and treated with nitrogen gas. The corresponding silyl enol ether is obtained by purification through a bulb tube distillation at 120°–140°/0.2 Torr.

b) 2.89 g (7.1 mmol) of the product obtained in a) are initially introduced with 5 ml of benzene and 47 mg (0.18 mmol) of bis-(acetylacetonato)-copper(II) complex (Cu (acac)$_2$) under a $N_2$ atmosphere. 1.40 g (14 mmol) of methyl diazoacetate in 15 ml of benzene are added to the mixture over a period of 3 hours whilst heating at 90°. After the evolution of nitrogen has ceased the solvent is removed, 0.5 g of aluminum oxide (neutral, activity III) is added to the residue and the mixture is filtered through a short column containing 7 g of aluminum oxide. The elution is carried out with pentane. For further purification the crude product is filtered once more through 10 g of $Al_2O_3$. The product is eluted with pentane and then with methyl tert.-butyl ether, from which the corresponding (S)-cyclopropane derivative is isolated.

c) A mixture of 1.38 g (2.5 mmol) of the cyclopropane derivative prepared in b), 20 ml of $CH_2Cl_2$ and 0.44 g (2.5 mmol) of $NEt_3 \cdot HF$ is stirred for approximately 1 hour. 15 ml of $H_2O$ are then added and the mixture is worked up by extraction with $CH_2Cl_2$. The crude product is purified by column chromatography on silica gel (elution with pentane/ethyl acetate=4/l) and subsequent crystallization from pentane with the addition of a little methyl tert.-butyl ether. Spectroscopically pure (S)-ketoester is obtained, which corresponds to the ketomethylene-analogue of (S)-Phe-Gly and has a m.p. of 58°-59°.

The complete course of the reaction is shown in diagram 1:

Diagram 1

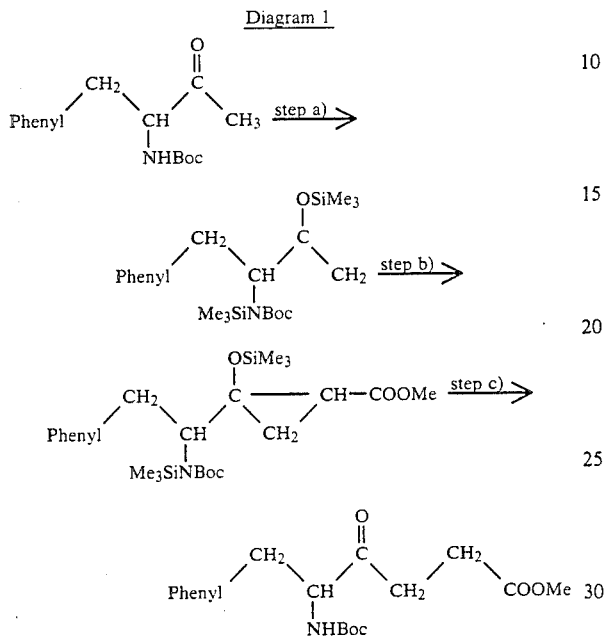

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages nd conditions.

What is claimed is:

1. A process for the enantiomer-selective preparation of γ-keto-δ-amino acid compounds of the formula I

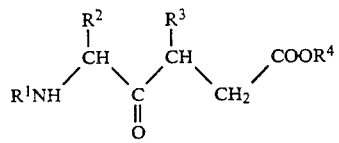

in which $R^1$ is an amino-protective group or H, $R^2$ is (1) an alkyl group having 1 to 5 C atoms, which can optionally be mono- or di-substituted by —OH, —COOH, —CONH$_2$ or —NH$_2$, (2) a $C_{1-5}$-alkyl group in which a CH$_2$ group is replaced by —S—, (3) phenyl or cyclohexyl which are unsubstituted or mono- or polysubstituted by alkyl or alkoxy containing 1 to 5 C atoms, halogen, hydroxyl or amino, (4) phenylalkyl, (5) cyclohexylalkyl, or (6) Het-alkyl-, where Het is a saturated or unsaturated 5- or 6-membered heterocyclic radical having 1-4 N atoms, which can be fused with a benzene ring, and -alkyl- is an alkylene group having 1-5 C atoms, and $R^3$ and $R^4$ are each independently H or alkyl having 1-5 C atoms, comprising:

(a) reacting a compound of the formula II

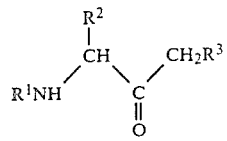

with a trialkylchlorosilane, to form a compound of the formula III

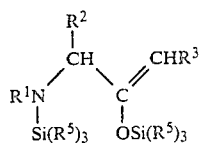

(b) reacting the compound of the formula III with a diazoacetate of the formula N$_2$CH$_2$COOR$^4$ ($R^4 \neq H$) to give a cyclopropane compound of the formula IV

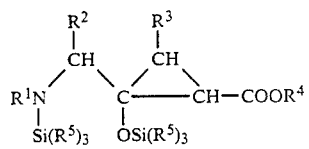

$R^5$ being an alkyl group having 1 to 5 C atoms, and (c) converting the compound of the formula IV by ring-opening and removal of the silyl groups into a compound of the formula I.

2. A process according to claim 1, further comprising saponifying the compound of formula IV so as to produce a compound of formula I.

3. A process according to claim 1, wherein (a) is conducted in the presence of an organic base.

4. A process according to claim 1, wherein (b) is conducted in the presence of a copper compound.

5. A process according to claim 4, wherein the copper compound is copper acetate, a copper halide, a bis-(salicyclaldiminato)-copper complex or a bis-(acetylacetonato)-copper (II) complex.

6. A process according to claim 1, wherein simultaneous ring opening and removal of silyl groups in (c) is performed by reacting the cyclopropane compounds of formula IV with a fluorine salt.

7. A process according to claim 6, wherein the fluorine salt is NaF, KF, (CH$_3$CH$_2$CH$_2$CH$_2$)$_4$NF or N(CH$_2$CH$_3$)$_3$·HF.

8. A process according to claim 7, wherein the reaction with the fluorine salt is conducted in the presence of an inert solvent.

9. A process of claim 8, wherein the solvent is dichloromethane or tetrachloromethane.

* * * * *